(12) United States Patent
Harper

(10) Patent No.: US 8,110,384 B2
(45) Date of Patent: Feb. 7, 2012

(54) PROCESS FOR CONVERSION OF DAIRY COW WASTE TO BIOFUEL PRODUCTS

(75) Inventor: Robert E. Harper, Bakersfield, CA (US)

(73) Assignee: KB Energy, LLC, Bakersfield, CA (US)

( * ) Notice: Subject to any disclaimer, the term of this patent is extended or adjusted under 35 U.S.C. 154(b) by 1058 days.

(21) Appl. No.: 11/962,801

(22) Filed: Dec. 21, 2007

(65) Prior Publication Data

US 2008/0153145 A1    Jun. 26, 2008

Related U.S. Application Data

(60) Provisional application No. 60/871,911, filed on Dec. 26, 2006.

(51) Int. Cl.
*C12P 7/06* (2006.01)
*C12P 7/08* (2006.01)
*C12P 7/10* (2006.01)
*C12P 5/00* (2006.01)
*C12P 1/04* (2006.01)
*C12P 1/02* (2006.01)
*C12P 7/14* (2006.01)

(52) U.S. Cl. ........ 435/165; 435/132; 435/161; 435/162; 435/163; 435/166; 435/170; 435/171

(58) Field of Classification Search .................. 435/132, 435/161–163, 165, 166, 170, 171
See application file for complete search history.

(56) References Cited

OTHER PUBLICATIONS

Palmqvist et al. 2000. Fermentation of Lignocellulosic hydrolysates. II: Inhibitors and Mechanism of inhibition. Bioresource Technology, vol. 74, pp. 25-33.*
Curiale, et al. 1976. Ribonucleic Acid Synthesized in Meiotic Cells of *Saccharomyces cerevisiae*: Effect of Culture Medium pH. Journal of Bacteriology, vol. 126, No. 2, pp. 661-667.*
Karns et al. 1995. Management of Microbial Processes in Cattle dippingVats Containing Coumaphos. Pesticide Science, vol. 45, pp. 13- 19.*

* cited by examiner

*Primary Examiner* — Sandra Saucier
*Assistant Examiner* — Kailash C Srivastava
(74) *Attorney, Agent, or Firm* — Kauth, Pomeroy, Peck & Bailey LLP

(57) ABSTRACT

A process and system for converting animal waste to useful biofuel products, and more particularly a process and system for converting excrement from lactating dairy cattle to a combination of ethanol, methane, carbon dioxide and fertilizer is presented. The system uses a continuous process to place the animal waste into an aqueous mixture with a starter sugar and a digestive microorganism into a heated anaerobic digester. The products of the reactions within the digester include methane, which is extracted in a gaseous form, and ethanol and carbon dioxide, which are separated out of an aqueous solution in a distillation column. The water from the solution is recycled and the solid residue remaining in the digester is dried in a rotary kiln and granulated to form a fertilizer material.

14 Claims, 1 Drawing Sheet

PROCESS FOR CONVERSION OF DAIRY COW WASTE TO BIOFUEL PRODUCTS

CROSS REFERENCE TO RELATED APPLICATION

This application claims priority to Provisional Application No. 60/871,911 filed Dec. 26, 2006, the disclosure of which is incorporated herein by reference.

FIELD OF THE INVENTION

The current invention is directed to a process and system for converting animal waste to useful biofuel products, and more particularly a process and system for converting manure and urine from lactating dairy cattle to a combination of cellulosic ethanol, conventional ethanol, methane, carbon dioxide and fertilizer.

BACKGROUND OF THE INVENTION

Modern dairies are very effective and efficient milk product producing facilities. Effectively, the days of a few dozen cows being milked by hand have become a part of history within the dairy industry. For example, today's commercial dairy has an average of about 1,000 lactating cows. In California's Kern County the average dairy has over 1,500 cows.

Milk handling and processing have been similarly industrialized. For example, in a modern dairy milking cows travel on paved floor paths to and from the milking parlor. Manure collected in these aisles, as well as in the milking parlor itself, is systematically washed down into a holding tank or lagoon and then disposed of by a variety of methods. Although a small amount of the manure is sold to neighboring farms or for commercial use as bagged manure, this is a very small percentage and therefore not very economical for the dairy. As a result, the disposal of this manure has become an environmental nightmare for areas of intensive dairy agriculture, as well as a regulatory nightmare for the farmers. In particular these large holding lagoons create noxious odors, they attract flies and present paths for the spread of pathogens both to the animals on the farm, as well as their human handlers and the general population.

In short, while the production end of a modern dairy is very efficient, the effluent end is not. Accordingly, a system is needed that will not only modernize the efficiency of manure waste disposal, but accomplish this in an economic and environmentally sound manner.

SUMMARY OF THE INVENTION

The current invention is directed to a process and system for converting animal waste to useful biofuel products, and more particularly a process and system for converting excrement from lactating dairy cattle to a combination of ethanol, methane, carbon dioxide and fertilizer.

In one embodiment of the invention, the system and process uses lactating dairy cow manure and urine as the feedstock.

In another embodiment of the invention, the system and process includes mixing the animal waste with an acid to allow for the break-down of cellulose material in the waste. In such an embodiment a 3% solution of sulfuric acid is used.

In still another embodiment of the invention, the system and process includes mixing the waste material with at least one sugar and at least one microorganism in an anaerobic digester. In such an embodiment, the sugar is preferably a 0.01% sugar solution and the microorganism is preferably *Saccharomyces cerevisiae*.

In yet another embodiment of the invention, the system and process includes heating the material in the anaerobic digester. In such an embodiment the temperature of the mixture is preferably raised to from about 84° F. and about 130° F.

In still yet another embodiment of the invention, the system and process includes extracting methane from the anaerobic digester in a gaseous form. Optionally the methane extraction may be aided by applying a vacuum to the methane outlet in the anaerobic digester.

In still yet another embodiment of the invention, the methane may be dried and compressed in an appropriate storage tank or used as a fuel to produce electricity through a generator.

In still yet another embodiment of the invention, the system and process includes separating the aqueous solution of water, carbon dioxide and ethanol into its components using a distillation column packed with activated carbon or other suitable medium. In such an embodiment the water may be re-used and the ethanol and carbon dioxide stored in appropriate tanks.

In still yet another embodiment of the invention, the system and process includes separating the solid residue from the anaerobic digester and converting the material to a fertilizer. In such an embodiment the conversion may include processing the solid residue in a rotary kiln and then granulating it to a desired size.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
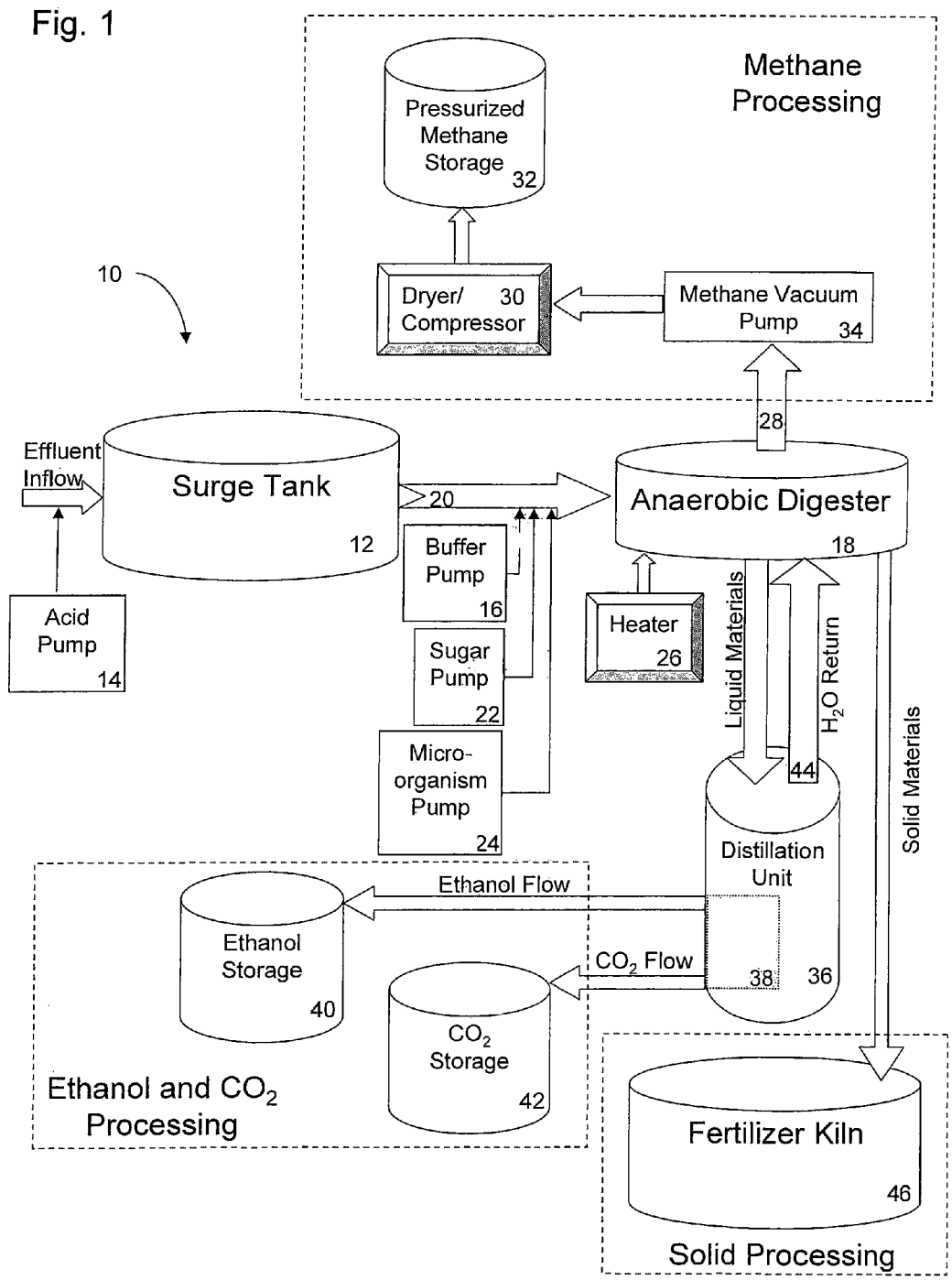
FIG. 1 provides a process flow chart of an embodiment of the animal waste conversion system of the current invention.

The current invention is directed to a process and system for converting lactating dairy cow animal waste to useful biofuel products, and more particularly a process and system for converting the combined output of manure and urine from lactating dairy cattle to a combination of ethanol, methane, carbon dioxide and fertilizer.

DEFINITION OF TERMS

The following terms are used herein:

"Excrement", "Manure" or "Waste" means the combination of feces and urine excreted from lactating dairy cows;

"Ethanol" means the chemical compound having the following molecular formula: $CH_3CH_2OH$;

"Methane" means the chemical compound having the following molecular formula: $CH_4$;

"Sugar" means any of the class of water-soluble crystalline carbohydrates, including sucrose and lactose, classified as monosaccharides, disaccharides, and trisaccharides, such as, for example, the compound having the following molecular formula: $C_{12}H_{22}O_{11}$;

"Water" means the chemical compound having the following molecular formula: $H_2O$;

"Acid means any of a class of compounds that form hydrogen ions when dissolved in water, and whose aqueous solutions react with bases and certain metals to form salts, such as, for example sulfuric acid, which is represented by the following molecular formula: $H_2SO_4$;

"Buffer" means any one of a number of products that has the ability to raise pH;

"Carbon Dioxide" means the chemical compound having the following molecular formula: $CO_2$;

"Fertilizer" means any of a large number of natural and synthetic materials, including manure and compounds containing nitrogen, phosphorus, and potassium, spread on or worked into soil to increase its capacity to support plant growth;

"Anaerobic Digester" means any closed vessel that contains no or only small concentrations of oxygen; and "Microorganism" means any anaerobic bacterium, fungus, mold or alga, or progeny thereof, which is capable of converting animal waste to a useful material in an anaerobic digester, such as, for example, *Saccharomyces cerevisiae*.

Process Description

It is well-known that animal waste can be used as a feedstock for the production of methane, it is further known that in some instances animal waste can also be converted into ethanol and other biofuels. (See, e.g., U.S. Pat. Nos. 629,774; 717,909; 5,411,594; 5,597,714; and 6,340,581; and U.S. Patent Publication Nos. 2006/0177916 and 2005/0266540, the disclosure of each of which are incorporated herein by reference.) However, to date the efficient conversion of animal waste to ethanol has not been achieved. The current invention provides a system and method for the conversion of animal waste having a particular composition of sugars, starches, cellulose and methane to produce a mixture of biofuels. More specifically, the current invention is directed to the conversion of the total waste output of lactating dairy cattle.

Lactating dairy cows expel between 120 to 140 lbs. of manure each day. Being a ruminant, dairy cows are somewhat efficient at digesting and converting nutritive materials to energy. Despite this relative efficiency, 3.2% of a dairy cow's body weight is excreted as undigested material in its waste. These nutritive materials that are excreted include grain and grain silage; sources of sugar, protein, and complex carbohydrates; and dry matter such as hay and straw. Moreover, these nutritive materials are carefully engineered, and in 50 to 60% of cases specially formulated by a nutritionalist to ensure the lactating cows have a well-balanced, high energy diet to provide optimum milk production. Table 1, below provides a detailed listing of the average content of the waste of dairy cattle manure. For the average lactating dairy cow of about 1,400 lbs., these values mean that about 44.8 lbs. of this specially formulate high grain, high sugar, complex carbohydrate, and dry matter feed-stuff composition is excreted undigested each day in the form of manure.

TABLE 1

Content of Dairy Cattle Manure

| Product | % of Manure |
|---|---|
| Water | 86.61 |
| Total Solids | 13.39 |
| Nitrogen | 2.9 |
| Phosphorus | 0.48 |
| Potassium | 2.86 |
| Carbon | 45.37 |
| Fiber | 52.6 |

While some of the elements and products above are essential for the metabolism of microorganisms that are used in the process, they serve no further purpose in the process and will remain with the sludge product after digestion. Specifically, of the above composition, it is the fiber that provides the supply of cellulose and hemicellulose, which can be degraded to mono-sugars that can then be used as a feedstock in the current process. The fiber of this manure stream is comprised of 12.2% Hemicellulose, 27.4% cellulose and 10.0% lignin.

The conversion of manure fiber, as well as other fibrous material to mono-sugars such as glucose and xylose was developed in the early 1900's. Various methods have been studied with two methods; enzymatic and acid hydrolysis being the preferred and most commonly used methods. However, never before has the composition of the manure itself been the subject of interest. For example, though many studies have been made of the waste from dairy farm operations, these studies have examined the overall output from all the cows in the farm, only a fraction of which will be lactating at any time. Specifically, in most dairy operations there will be, in addition to the lactating cows, a large population of non-lactating animals, both adult and juvenile. As a result, the indiscriminant use of animal waste from dairy operations, such as is described in conventional processes, inherently includes the use of waste from these non-lactating cows, which in turn results in the loss of the efficiency advantages described in the current application. In addition, most of the prior art processes only use the solid manure product and discard the urine. As a result the ultimate efficiency of these processes have not been improved significantly over the years.

Now it has been surprisingly discovered that, as a result of the special diet and peculiar physiology of lactating cows, the total excrement from these animals, both manure and urine, when property processed and combined with water, a "starter" sugar, and the appropriate mixture of microorganisms in an anaerobic condition, can both efficiently and economically produce a mixture of biofuels including methane, carbon dioxide, and ethanol. The key to this process is the use of excrement exclusively from lactating dairy cows, and the use of both the manure and urine from those cows. The unique composition of hormones and sugars in these materials makes the greater efficiencies of conversion possible. Specifically, the current process is capable of converting at least 30%, more preferably 40%, and even more preferably at least 50% of the total excrement feedstock from a lactating dairy cow into an ethanol product.

FIG. 1. shows one exemplary embodiment of a process system (10) for producing biofuels, including ethanol from lactating dairy cattle waste. As shown in the diagram, in a first step the waste manure, which is washed down from the dairy is collected in a surge tank (12) as a slurry mixture of solid manure, urine and water.

As this slurry is being pumped into the surge tank a weak solution of acid is mixed in with the effluent (14) to increase the speed of the breakdown of cellulose materials. In one preferred embodiment, the acid is a 3% solution of sulfuric acid. The importance of this step lies in the composition of the untreated manure.

As discussed above, one of the major components of most manure is lignocellulose material. Lignocellulose materials are complex cellulose materials that are found in straw, legumes such as hay, and other dry matter that is typically found in conventional cattle feeds. The fiber in manure has already undergone some breakdown (enzymatic hydrolysis) while in the dairy cows digestive tract. The pretreatment helps to further break down this material. However, in addition to breaking down these materials for better processing, this pretreatment also produces additional sugars from the manure.

At this point the hemicellulose of the now semi-processed manure is completely degraded into arabinose, glucose and xylose. The optimal hydrolysis process yields an additional 11.32 g/100 g manure or a 40% conversion rate of cellulosic material.

This pretreatment process takes about one hour to complete, at the end of which one obtains a feedstock solution comprised of various sugars, and mainly glucose, xylose and others. At the end of the pretreatment, a buffering agent (16) is injected into the pretreated feedstock material to increase the pH of the mixture back to around 7, or a neutral pH. This neutralization is important to ensure an environment conducive to microorganism activity.

Once the pretreated material is neutralized, the mixture then enters an anaerobic digester (18) via a pipeline (20). During transit to the anaerobic digester, the pretreated material is injected with a starter sugar solution (22) (from any available source) and at least one microorganism (24). Although a sugar solution from any available source may be used, in a preferred embodiment the sugar source is in a solution concentration of 0.01%. Likewise, although any combination of microorganisms capable of producing ethanol may be used, in one preferred one of the microorganisms is *Saccharomyces cerevisiae*.

Hydrolysis continues until the slurry mixture enters the anaerobic digester and encounters process heat at which point it ceases. The heat is applied to the vessel by any conventional means. Although any heat level suitable for activating the microorganism may be used, in a preferred embodiment temperature is raised to a range between about 84° F. and about 130° F. The heat and the available starter sugar "wake" the *Saccharomyces cerevisiae* or other microorganism, making it active and beginning its life cycle. During its life cycle, the microorganism grows and reproduces in the tack of oxygen and the presence of warmth and nourishment. As this fermentation process occurs, two excretions or by-products from the microorganism are produced: ethanol and carbon dioxide. Both of these products are soluble in water and as such create no pressure or vapor within the anaerobic digester.

Concurrent with this primary fermentation process additional reactions occur, which both enhance the production of ethanol and carbon dioxide, and produce other by-products such as methane gas. For example, simultaneous with the break-down of the "starter" sugars, additional sugars are being created by the decomposition of the organic matter within the digester. These sugars will also be consumed by the microorganisms, as well as some naturally occurring enzymes and microorganisms that are excreted from the cow's digestive system along with the manure. These sugars and the natural fermentation process will add some additional ethanol, $CO_2$ and methane. In addition, manure already naturally contains quantities of methane, although the concentration of methane changes depending on the feed used.

According to a study published by the Purdue University, Agricultural Engineering Department, the biogas produced in anaerobic digesters is typically about 60 to 70% methane, and can be easily harvested. In the current system this methane is collected from the digester through an outlet (28) at the top of the digester vessel. The gas is then sent to a dryer/compressor unit (30) which processes it for storage in a pressure vessel (32) for use or sale. To enhance the removal of the methane gas suction, such as by a vacuum pump (34) may be applied to the outlet (28) at the top of the vessel. As discussed previously, although carbon dioxide is a gas, it will stay in solution with the water and can be separated in a later step to avoid contamination of the methane gas.

There are a number of advantages to the current system. First, from an environmental perspective both methane and carbon dioxide are known greenhouse gases with methane containing about 20 times more releasable energy than $CO_2$. Where manure is being stored and exposed to the atmosphere, methane is naturally escaping and effecting air quality. The use of the current system reduces odor by up to 90% and also eliminates the release of greenhouse gas emissions. Moreover, using the current digester system those greenhouse gases may be captured and used to create energetic materials that can then be used for electrical co-generation. As an example, the Minnesota Department of Agriculture calculates that a 500 cow dairy utilizing an anaerobic digester can produce enough methane to generate about 2,000 KWH of electricity per day. That amount of electricity is sufficient to address the energy consumption of the dairy and provide an excess that can be sold back to the local energy company. Finally, the digester also destroys some if not all of the pathogens associated with manure reducing the health risks associated with open lagoons of stored animal waste.

Returning to the inventive process, at this stage the digester is producing a mixture of ethanol, carbon dioxide and methane. As discussed above, the methane is being harvested from the digester, dried and stored in a pressure vessel or utilized for energy production. Within the digester, however, there is still an aqueous solution of ethanol and carbon dioxide that must be separated from the water and stored. As shown, in the current process system this separation is carried out by a distillation column (36), which is in fluid communication with the digester. The distillation column is a cylinder containing a filtrate material (38) capable of separating the water from the ethanol and the carbon dioxide. The ethanol, which is in a liquid form, and the carbon dioxide, which is a gas, are then pumped to separate vessels (40 and 42) for storage. The water can be recycled (44) for use in the next batch process, or desalinated and returned to the farm for use in irrigation.

Finally, once all of the liquid products are removed from the digester a quantity of concentrated organic solid material remains. This nitrogen rich material is a perfect feedstock for fertilizer production. As such, in one embodiment the solid material is removed and transported to a rotary kiln (46) where it is injected with a slight amount of clay, dried and granulated into fertilizer. Once the product has been dried and sized it can be stored as a bulk commodity or bagged for sales.

EXAMPLES

Experiments were conducted to test the efficiency of the inventive system. All samples were collected under stringent controls, and an independent certified laboratory was used for analysis of the results.

The testing apparatus consisted of several equally-sized glass containers filled with a mixture of manure, water, sugar and at least one microorganism. Different cultures of microorganisms were examined for efficiency and though *Saccharomyces cerevisiae* showed particularly good efficacy, several work equally well.

During testing, each sample was agitated for 15 seconds and an air tight seal of paraffin was then applied to completely fill the vessels, replacing any oxygen, thereby producing an anaerobic condition within the test vessel. Above the paraffin an air tight seat was placed as a second method of ensuring anaerobic conditions. The vessels were then allowed to mature for a specified amount of time and then placed in complete darkness. All other factors, such as volume, temperature and other stimuli were held constant and identical for all samples.

After the set period of time the vessels were re-exposed to sunlight, the seals were broken and the experiment was stopped. Each vessel was then sampled and the sample placed in an identical, clean vessel for transport to the laboratory for analysis.

Qualitative Analysis:

The results obtained from the analysis were examined using chromatographic analysis, (ATSM D-1945-96, ATSM D-3588-89 and GPA 2145-94). The qualitative results showed the following products: 4100 mg/L of ethanol in solution, 0.589% of methane in solution by weight, 24.601% of carbon dioxide in solution by weight and 55.616% of nitrogen in solution by weight. As discussed above, these were qualitative tests carried out to prove that the products mentioned above can indeed be derived from the manure of lactating dairy cows.

Quantitative Analysis:

Analysis shows that ethanol of a sufficient quality to be mixed with any grade of unleaded gasoline to produce the product E-85 is produced by this process. In one embodiment of the invention the efficiency of this process is preferably >30% and even more preferably around 60% due to the presence of xylose and other fractions of the slurry that will not be utilized in this part of the process.

Ethanol Production

It is known from prior research that the production of ethanol from corn as a raw product or feed stock yields 2.5 U.S. gallons of ethanol per bushel of corn. One bushel of corn is equal to 56 pounds of corn. Using the calculated efficiencies discussed above, the amount of usable ethanol obtainable from one cow per day can be determined. For example, one lactating dairy cow will excrete 120-140 pounds per day of manure. Of that manure to 32 to 38% of the feed material is not digested, amounting to a mass of about 38.4 to 53.2 pounds per day per cow of material that can be processed by the system of the current invention. It is considered preferable that at least 30%, more preferably 40%, and even more preferably at least 50% but less than 60% of the total manure feedstock is converted by chemical and microorganism activities and reactions into the ethanol product.

Using the above process and system, and the cited conversion factors it can be shown that the untreated manure from lactating dairy cows can be altered from its original form to provide for over 210 grams per hour of glucose and other sugars from each cow. This FIGURE is obtained from a simple calculation of the various possible sources of glucose from the cow.

For example, glucose is produced in the cow's excreted waste at 130 g/hr, from the cow's urine at 12.5 g/hr, and from the cellulosic fiber contained in the cow's waste at 13.5 g/hr. Other sugars are likewise produced at a rate of 58.0 g/hr. In short, out of a total of 54,430 grams of total manure excreted per cow per day the process of the current invention is able to produce/capture a (minimum) total of over 5,040 grams per day of glucose (and other sugars) in the total fecal matter. Using standard conversion factors and keeping in mind the conversion efficiency rate of the current process of 60%, there is enough glucose to produce between 1.5 to 2.5 gallons of 90% pure ethanol per cow per day under normal fermentation practices. The above numbers are based on USDA information based on a 1000 pound lactating dairy cow. This level of glucose production is unique to lactating dairy cows and allows for a substantially greater conversion of manure to ethanol.

Methane Production

Methane is a by-product of lactating dairy cow manure, as a result of enteric fermentation. Methane is also one of the products of decomposition of manure by an anaerobic digester. By combination of these two reactions the harvested methane from the current process was measured at 0.589% by weight of the final product. Based on such a percent conversion, as will be described in detail below, it is believed that sufficient amounts of methane will be produced by the inventive process for sustaining a dairy plant having an average number of cows per acre, with any excess being available for sale.

Various University, government and industry studies concur that a healthy lactating dairy cow releases a mean average of 587 liters of methane per day. Although no process can capture all of this methane, some percentage of which is released through normal flatulence in to atmosphere, calculations indicate that the current system and process will be able to capture and/or contain 67% of the 78.5 cu. ft. of biogas methane per cow or 851,725 cu. ft. for a herd of 17,500 lactating cows. Once the methane is stripped of the contaminating gases trapped within the biogas, enough methane can be stored to produce a theoretical yield of 59.5 megawatts of electricity per day. Based on the known efficiencies of various methane or natural gas turbine manufactures, which vary from 57% to 66% based on when the turbine was manufactured, newer technologies being more efficient, a practical level of 32 megawatts can be generated per day. Accordingly, the current system produces 3.4 kilowatts of electricity per 120 pounds of manure.

A shown in Table 2, below, the plant requirement for the current system will vary from 6 to 8 megawatts per day. Ambient temperature, lighting, desalination, heat requirements, distillation all play a role in the consumption of power per day.

TABLE 2

Total Plant Consumption (Maximum Energy Usage Conditions)

| Equipment Required | Kilowatts Required |
|---|---|
| Electric Pumps | 3520 |
| Drier/compressor | 465 |
| Tank heat | 530 |
| Tank mix | 120 |
| Fertilizer Kiln | 1680 |
| Desalinization | 500 |
| Piping Hydraulics | 340 |
| Lighting/Office | 280 |
| Laboratory | 330 |
| Process Controls | 260 |
| Miscellaneous | 250 |
| Total megawatts per day | 8.272 |

Carbon Dioxide Production

Laboratory results also indicated that carbon dioxide levels in the sample were 24.601%. As discussed above, this carbon dioxide product can be harvested and either compressed to form dry ice or sold as a gas.

Fertilizer Production

To calculate the total amount of waste product and fertilizer produced by the plant we must first make an assumption about the amount of waste to be processed on average. For example, a plant that receives 2.1 million gallons of wet manure per day with a ratio of manure to water of no greater than 20% manure to 80% water will produce the following levels of waste and fertilizer by-product. First, in such a scenario the total solid content of the manure is 13.39% for a daily total of 281,190 pounds of total solids entering the process. The fiber in this material is being converted to glucose removing 52.6% and leaving 47.4% of the total solids or 133,284 pounds. This material will be injected with a clay, introduced into the fertilizer kiln operating 220° F. to evaporate the water, destroy any *e-coli* or *salmonella* contamination and form a usable fertilizer product. On average the content of this material will be 3 parts Nitrogen, 0.5 parts Phosphate, 2.5 parts Potassium and minor plant nutrition elements such as Sulfur, Iron and Zinc.

Although specific embodiments are disclosed herein, it is expected that persons skilled in the art can and will design alternative animal waste conversion systems and processes that are within the scope of the following claims either literally or under the Doctrine of Equivalents.

What is claimed is:

1. A process for converting animal waste into useable biofuel materials comprising:
   providing a source of waste slurry comprising a mixture of water and excrement from lactating cows;
   mixing said slurry with an acid to acidify the slurry;
   holding said slurry and acid mixture in a surge tank for a period of time sufficient to substantially break down any cellulose materials within said slurry to form a pretreated material;
   mixing a neutralizer into said pretreated material to form a neutralized pretreated material;
   mixing starter sugar and a microorganism, wherein said microorganism is *Saccharomyces cerevisiae* into said neutralized pretreated material to form a feedstock;
   introducing said feedstock into an anaerobic digester;
   heating said feedstock to a temperature such that said microorganism is activated to begin fermentation of said feedstock to produce at least ethanol and methane as products; and
   collecting the products of said fermentation.

2. The process of claim 1, wherein the ethanol is in solution with at least carbon dioxide and water contaminants, the process further comprising distilling said solution to separate said ethanol from said carbon dioxide and water contaminants.

3. The process of claim 2, further comprising collecting the separated carbon dioxide and ethanol in separate storage containers.

4. The process of claim 2, further comprising reintroducing said water to said anaerobic digester.

5. The process of claim 2, wherein said distilling purifies said ethanol by at least 90%.

6. The process of claim 1, further comprising drying and compressing said methane prior to storage.

7. The process of claim 1, further comprising applying a positive suction to said anaerobic digester to collect said methane.

8. The process of claim 1, further comprising collecting all solid organic material from said anaerobic digester.

9. The process of claim 8, further comprising drying and granulating said solid organic material to form fertilizer.

10. The process of claim 1, further comprising desalinating any waste water produced from said process prior to release.

11. The process of claim 1, wherein said heating heats said anaerobic digester to a temperature between about 85° F. and 130° F.

12. The process of claim 1, wherein the acid is a 3% solution of sulfuric acid.

13. The process of claim 1, wherein the neutralizer is a buffering agent capable of increasing the pH of the pretreated material to around 7.

14. The process of claim 1, wherein the starter sugar is in a solution concentration of 0.1%.

* * * * *